United States Patent [19]

Mikkelsen

[11] Patent Number: Plant 5,533

[45] Date of Patent: Aug. 13, 1985

[54] KLANCHOE PLANT NAMED CITATION

[75] Inventor: James C. Mikkelsen, Ashtabula, Ohio

[73] Assignee: Mikkelsens, Inc., Ashtabula, Ohio

[21] Appl. No.: 554,708

[22] Filed: Nov. 23, 1983

[51] Int. Cl.[3] ..... A01H 5/00

[52] U.S. Cl. ..... Plt./68

[58] Field of Search ..... Plt./68

*Primary Examiner*—Robert E. Bagwill

*Attorney, Agent, or Firm*—Schwartz, Jeffery, Schwaab, Mack, Blumenthal & Koch

[57] ABSTRACT

A new and distinct cultivar of kalanchoe plant named Citation characterized by its pink flower color with salmon overtones and white throat, uniform flowering, excellent self-branching, excellent keeping qualities, adaptability to various pot sizes, and by its complimenting the genetically related cultivars Sensation, Dignity and Royalty.

2 Drawing Figures

1

The present invention relates to a new and distinctive cultivar of kalanchoe plant, botanically known as *Kalanchoe blossfeldiana Poelln,* and known by the cultivar name Citation. The new cultivar was discovered by me as a mutation of the cultivar Sensation, disclosed in U.S. Plant Pat. No. 4,727. The mutation was found on several different occasions in flowering crops of 10 cm. pots of the parent cultivar, indicating that a particular stock plant had an axiallary shoot that mutated and was the source of the several indentical mutant plants.

Asexual reproduction of stem cuttings has shown that the unique features of this new kalanchoe are stabilized and are reproduced true to type in sucessive propagations.

The following characteristics distinguish the new kalanchoe from both its parent cultivar and other cultivated kalanchoes of this type known and used in the floriculture industry:

1. Citation is a color mutation of Sensation, having lighter pink flowers with a tinge of orange in the petals as they mature. The new cultivar has a yellow/cream to nearly white throat or eye in the center of corolla.

2. The flower color of Citation is a darker pink than Dignity, also a mutation of Sensation and disclosed in my pending application Ser. No. 422,521. The new cultivar is somewhat more self-branching than Dignity, thus appearing to be more floriferous.

3. As Citation matures, the flower color becomes considerably lighter, with more salmon or orange overtones.

4. In comparison to the red flower color of Royalty, also a mutation of Sensation and disclosed in my pending application Ser. No. 422,150, the flower color of the new cultivar is dark pink.

5. In further comparing Citation to the original parent Sensation, excepting for the flower color differnces, all other characteristics of a morphological and physiological nature are nearly the same.

The accompanying colored photographs were taken Nov. 5, 1983, and illustrate in perpsective view the overall appearance of Citation, showing the colors as true as it is reasonably possible to obtain in a colored reproductions of this type. The upper photograph is of Citation, and the lower photograph comprises a composite photograph of Citation, Sensation, Dignity, and Royalty, illustrating the color variations between the four related cultivars.

2

The following is a detailed description of my new kalanchoe cultivar based on plants produced under commercial practices in 10 cm. plastic pots grown at Mikkelsens Inc., Ashtabula, Ohio 44004. Color references are made to The Royal Horticultural Society Colour Chart except where general terms of ordinary dictionary significance are used Parentage:

A flower color mutation of the cultivar Sensation.

Propagation:

(A) *Type cutting.*—Short tip cutting, with stems up to 2 cm. long.

(B) *Time to root.*—10 days at 21° C. summer, 14 days at 21° C. winter.

(C) *Rooting habit.*—Many very fine roots, fibrous.

Plant description:

(A) *Form.*—Short, compact, upright growth. Growing and scheduling practices can produce a small plant in a 10 cm. pot up to a larger plant in a 15 cm. pot.

(B) *Habit of growth.*—Rate of growth moderate for this type of plant. Generally, shoots are formed at every node.

(C) *Foliage description.*—Leaves simple, opposite. Frequently, leaves are asymmetrical, with a slight tendency to bend or twist. (1) Size: Average full grown leaf 130 mm. long×80 mm. wide. Full grown leaves have petioles up to 30 mm. long; young leaves have short petioles. (2) Shape: Ovate to elliptic, apex obtuse, base attenuate. (3) Texture: Glabrous, coriaceous, succulent. (4) Margin: Sinuate to crenate. (5) Color: Young foliage, top side green 137B, under side green 138A. Mature foliage, top side darker than green 137A to yellow green 147A, under side green 137A-B.

Flowering description:

(A) *Flowering habits.*—Inflorescence of each shoot is formed by dichotomous branching, starting with opening of terminal flower of main axis, followed by terminal flowers of the side branches, continuing with subsequent development of branches in the inflorescence. Opening of new buds will continue for two months or more. Individual flowers last two weeks or more after opening.

(B) *Natural flowering season.*—Late January Flowering time under controlled daylength at 20° C. in summer is 10 weeks; in winter 14 weeks. Flowering time depends on temperature, light intensity and other growing conditions.

(C) *Flower bud description.*—Elliptical to oblong, up to 8 mm. long, developing to tubular as flower petals mature, sheathed with four green sepals. Corolla at maturity, 8 mm. long.

(D) *Flowers borne.*—Compound dichasial cyme on strong peduncles. Primary peduncle is 5 mm. in diameter, with peduncle length depending on growing conditions and B9 application; pedicels up to 8 mm. long.

(E) *Quantity of flowers.*—Highly floriferous. Main axis and side shoots have 100 or more flowers.

(F) *Petals.*—(1) Shape: Nearly round, with apex slightly cuspidate. (2) Color: Top side when opening red 52B, fading to red 52C, with light cream to white throat in center of corolla; under side from red 49A to 52D. (3) Number of petals:

Four (4) united in corolla, salverform; 6 mm. in diameter; total flower diameter is 16 mm .

(G) *Reproductive organs.*—(1) Stamens: Eight (8) in number. (a) Anther shape: Flat, elliptical, color light brown, frequently degenerate. (b) Filament color: Light green. (c) Pollen color: Yellow. (2) Pistels (a) Stigma: Flat, crystalline, color greenish white. (b) Styles: Light green in color. (c) Ovaries: 4 celled, 6 mm. long, color green 143A.

Disease resistance: No diseases or adverse physiological problems observed to date. Cultivar is highly resistant to mildew.

I claim:

1. A new and distinct cultivar of kalanchoe plant named Citation, as illustrated and described, and characterized by its pink flower color with salmon overtones and white throat, uniform flowering, excellent self-branching, excellent keeping qualities, adaptability to various pot sizes, and by its complimentingthe genetically related cultivars Sensation, Dignity and Royalty.

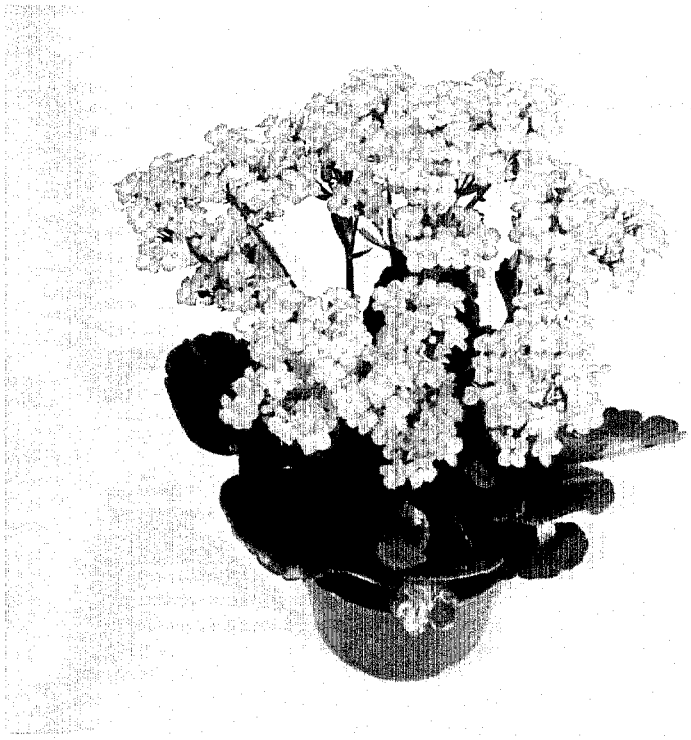
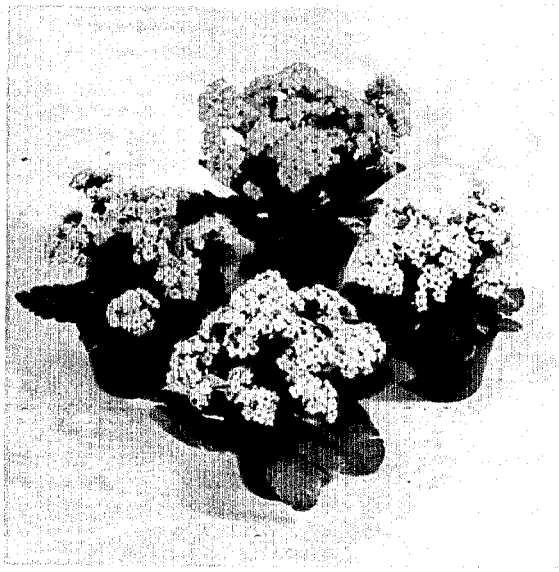

* * * * *